US009386909B2

(12) United States Patent
Fengler et al.

(10) Patent No.: US 9,386,909 B2
(45) Date of Patent: Jul. 12, 2016

(54) SYSTEM AND METHOD FOR DEPOSITION AND REMOVAL OF AN OPTICAL ELEMENT ON AN ENDOSCOPE OBJECTIVE

(71) Applicant: Novadaq Tecnologies Inc., Mississauga (CA)

(72) Inventors: John Fengler, North Vancouver (CA); John Senger, Vancouver (CA); Gary Jenne, Aldergrove (CA)

(73) Assignee: Novadaq Technologies Inc., Mississauga (CA)

( * ) Notice: Subject to any disclaimer, the term of this patent is extended or adjusted under 35 U.S.C. 154(b) by 302 days.

(21) Appl. No.: 13/853,656

(22) Filed: Mar. 29, 2013

(65) Prior Publication Data
US 2013/0237762 A1    Sep. 12, 2013

Related U.S. Application Data

(62) Division of application No. 11/830,323, filed on Jul. 30, 2007, now Pat. No. 8,408,269.

(60) Provisional application No. 60/833,897, filed on Jul. 28, 2006.

(51) Int. Cl.
*A61B 1/00* (2006.01)
*A61B 1/05* (2006.01)
(Continued)

(52) U.S. Cl.
CPC .......... *A61B 1/00101* (2013.01); *A61B 1/0011* (2013.01); *A61B 1/00096* (2013.01); *A61B 1/00126* (2013.01); *A61B 1/00144* (2013.01);
(Continued)

(58) Field of Classification Search
CPC .......... A61B 1/00096; A61B 1/00101; A61B 1/0011; A61B 1/00126; A61B 1/00144; A61B 1/00186; A61B 1/042; A61B 1/043; A61B 1/05; A61B 1/0646; Y10T 156/17; Y10T 156/1798; Y10T 156/18
USPC ....................... 156/290, 556, 580, 581, 308.2
See application file for complete search history.

(56) References Cited

U.S. PATENT DOCUMENTS 3,215,029 A * 11/1965 Woodcock .................... 385/116
3,971,068 A    7/1976 Gerhardt et al.
(Continued)

FOREIGN PATENT DOCUMENTS

DE    195 35 114 A1    3/1996
DE    196 08 027 A1    9/1996
(Continued)

OTHER PUBLICATIONS

Final Office Action mailed on Jul. 23, 2008, for U.S. Appl. No. 11/122,267 (6 pages).
(Continued)

*Primary Examiner* — Sonya Mazumdar
(74) *Attorney, Agent, or Firm* — Morrison & Foerster LLP

(57) ABSTRACT

An applicator suitable for converting a white-light endoscope into an endoscope for combined white-light/fluorescence imaging is disclosed. The applicator facilitates attachment of an optical element, for example an optical filter, to a distal optical port of an endoscope. The applicator engages with alignment feature on the endoscope's distal end and releasably supports the optical element in an opening that is aligned with the optical port. The optical element is released in a proximal direction by pressing down on an actuator.

7 Claims, 12 Drawing Sheets

(51) Int. Cl.
　　*B29C 65/48*　　　　(2006.01)
　　*B32B 37/10*　　　　(2006.01)
　　*A61B 1/04*　　　　(2006.01)
　　*A61B 1/06*　　　　(2006.01)
　　*B29C 65/58*　　　　(2006.01)

(52) U.S. Cl.
　　CPC ............. *A61B 1/00186* (2013.01); *A61B 1/042* (2013.01); *A61B 1/043* (2013.01); *A61B 1/05* (2013.01); *A61B 1/0646* (2013.01); *Y10T 156/17* (2015.01); *Y10T 156/1798* (2015.01); *Y10T 156/18* (2015.01)

(56) References Cited

U.S. PATENT DOCUMENTS

| | | |
|---|---|---|
| 4,037,866 A | 7/1977 | Price |
| 4,066,330 A * | 1/1978 | Jones ............................ 359/503 |
| 4,115,812 A | 9/1978 | Akatsu |
| 4,149,190 A | 4/1979 | Wessler et al. |
| 4,200,801 A | 4/1980 | Schuresko |
| 4,318,395 A * | 3/1982 | Tawara ........................ 600/112 |
| 4,355,325 A | 10/1982 | Nakamura et al. |
| 4,378,571 A | 3/1983 | Handy |
| 4,449,535 A | 5/1984 | Renault |
| 4,471,766 A * | 9/1984 | Terayama ..................... 600/104 |
| 4,532,918 A | 8/1985 | Wheeler |
| 4,556,057 A | 12/1985 | Hiruma et al. |
| 4,611,888 A | 9/1986 | Prenovitz et al. |
| 4,638,365 A | 1/1987 | Kato |
| 4,660,982 A * | 4/1987 | Okada ........................... 356/636 |
| 4,768,513 A | 9/1988 | Suzuki |
| 4,786,813 A | 11/1988 | Svanberg et al. |
| 4,821,117 A | 4/1989 | Sekiguchi |
| 4,837,625 A | 6/1989 | Douziech et al. |
| 4,856,495 A | 8/1989 | Tohjoh et al. |
| 4,895,145 A | 1/1990 | Joffe |
| 4,930,516 A | 6/1990 | Alfano et al. |
| 4,951,135 A | 8/1990 | Sasagawa et al. |
| 4,954,897 A | 9/1990 | Ejima et al. |
| 4,974,936 A | 12/1990 | Ams et al. |
| 5,001,556 A | 3/1991 | Nakamura et al. |
| 5,007,408 A | 4/1991 | Ieoka |
| 5,034,888 A | 7/1991 | Uehara et al. |
| 5,134,662 A | 7/1992 | Bacus et al. |
| 5,165,079 A | 11/1992 | Schulz-Hennig |
| 5,205,280 A * | 4/1993 | Dennison et al. ............. 600/112 |
| 5,214,503 A | 5/1993 | Chiu et al. |
| 5,225,883 A | 7/1993 | Carter et al. |
| 5,255,087 A | 10/1993 | Nakamura et al. |
| 5,278,642 A | 1/1994 | Danna et al. |
| 5,365,057 A | 11/1994 | Morley et al. |
| 5,371,355 A | 12/1994 | Wodecki |
| 5,377,686 A | 1/1995 | O'Rourke et al. |
| 5,408,263 A | 4/1995 | Kikuchi et al. |
| 5,410,363 A | 4/1995 | Capen et al. |
| 5,419,323 A | 5/1995 | Kittrell et al. |
| 5,420,628 A | 5/1995 | Poulsen et al. |
| 5,421,337 A | 6/1995 | Richards-Kortum et al. |
| 5,424,841 A | 6/1995 | Van Gelder et al. |
| 5,430,476 A | 7/1995 | Hafele et al. |
| 5,485,203 A | 1/1996 | Nakamura et al. |
| 5,490,015 A | 2/1996 | Umeyama et al. |
| 5,507,287 A | 4/1996 | Palcic et al. |
| 5,536,236 A | 7/1996 | Yabe et al. |
| 5,585,846 A | 12/1996 | Kim |
| 5,590,660 A | 1/1997 | MacAulay et al. |
| 5,596,654 A | 1/1997 | Tanaka |
| 5,646,680 A | 7/1997 | Yajima |
| 5,647,368 A | 7/1997 | Zeng et al. |
| 5,647,840 A | 7/1997 | D'Amelio et al. |
| 5,667,472 A | 9/1997 | Finn et al. |
| 5,695,049 A | 12/1997 | Bauman |
| 5,697,373 A | 12/1997 | Richards-Kortum et al. |
| 5,713,364 A | 2/1998 | DeBaryshe et al. |
| 5,749,830 A | 5/1998 | Kaneko et al. |
| 5,772,355 A | 6/1998 | Ross et al. |
| 5,772,580 A | 6/1998 | Utsui et al. |
| 5,827,190 A | 10/1998 | Palcic et al. |
| 5,833,617 A | 11/1998 | Hayashi |
| 5,852,498 A | 12/1998 | Youvan et al. |
| 5,891,016 A | 4/1999 | Utsui et al. |
| 5,897,269 A | 4/1999 | Ross et al. |
| 5,971,918 A | 10/1999 | Zanger |
| 5,984,861 A | 11/1999 | Crowley |
| 5,986,271 A | 11/1999 | Lazarev et al. |
| 5,990,996 A | 11/1999 | Sharp |
| 5,999,240 A | 12/1999 | Sharp et al. |
| 6,002,137 A | 12/1999 | Hayashi |
| 6,004,263 A | 12/1999 | Nakaichi et al. |
| 6,008,889 A | 12/1999 | Zeng et al. |
| 6,021,344 A | 2/2000 | Lui et al. |
| 6,028,622 A | 2/2000 | Suzuki |
| 6,059,720 A | 5/2000 | Furusawa et al. |
| 6,061,591 A | 5/2000 | Freitag et al. |
| 6,069,689 A | 5/2000 | Zeng et al. |
| 6,070,096 A | 5/2000 | Hayashi |
| 6,095,982 A | 8/2000 | Richards-Kortum et al. |
| 6,099,466 A | 8/2000 | Sano et al. |
| 6,110,106 A | 8/2000 | MacKinnon et al. |
| 6,120,435 A | 9/2000 | Eino |
| 6,148,227 A | 11/2000 | Wagnieres et al. |
| 6,161,035 A | 12/2000 | Furusawa |
| 6,192,267 B1 | 2/2001 | Scherninski et al. |
| 6,212,425 B1 | 4/2001 | Irion et al. |
| 6,258,576 B1 | 7/2001 | Richards-Kortum et al. |
| 6,280,378 B1 | 8/2001 | Kazuhiro et al. |
| 6,293,911 B1 | 9/2001 | Imaizumi et al. |
| 6,332,092 B1 | 12/2001 | Deckert et al. |
| 6,364,829 B1 | 4/2002 | Fulghum |
| 6,364,831 B1 | 4/2002 | Crowley |
| 6,419,628 B1 | 7/2002 | Rudischhauser et al. |
| 6,422,994 B1 | 7/2002 | Kaneko et al. |
| 6,526,213 B1 | 2/2003 | Ilenda et al. |
| 6,529,768 B1 | 3/2003 | Hakamata |
| 6,537,211 B1 | 3/2003 | Wang et al. |
| 6,544,102 B2 * | 4/2003 | Schafer et al. ..................... 451/5 |
| 6,603,552 B1 | 8/2003 | Cline et al. |
| 6,639,664 B2 | 10/2003 | Haan et al. |
| 6,772,003 B2 | 8/2004 | Kaneko et al. |
| 6,773,392 B2 | 8/2004 | Kikuchi et al. |
| 6,786,865 B2 | 9/2004 | Dhindsa |
| 6,821,245 B2 | 11/2004 | Cline et al. |
| 6,898,458 B2 | 5/2005 | Zeng et al. |
| 6,899,675 B2 | 5/2005 | Cline et al. |
| 6,960,165 B2 | 11/2005 | Ueno et al. |
| 7,043,291 B2 | 5/2006 | Sendai |
| 7,235,045 B2 | 6/2007 | Wang et al. |
| 7,236,815 B2 | 6/2007 | Richards-Kortum et al. |
| 7,324,674 B2 | 1/2008 | Ozawa et al. |
| 7,341,557 B2 | 3/2008 | Cline et al. |
| 7,385,772 B2 * | 6/2008 | Forkey et al. ................. 359/819 |
| 7,704,206 B2 | 4/2010 | Suzuki et al. |
| 7,722,534 B2 | 5/2010 | Cline et al. |
| 7,798,955 B2 | 9/2010 | Ishihara et al. |
| 8,408,269 B2 | 4/2013 | Fengler et al. |
| 8,630,698 B2 | 1/2014 | Fengler et al. |
| 8,961,403 B2 | 2/2015 | Cline et al. |
| 2001/0016679 A1 | 8/2001 | Futatsugi et al. |
| 2002/0035330 A1 | 3/2002 | Cline et al. |
| 2002/0138008 A1 | 9/2002 | Tsujita et al. |
| 2002/0161284 A1 | 10/2002 | Sendai |
| 2002/0161284 A1 * | 10/2002 | Tanaka ........................ 600/176 |
| 2002/0175993 A1 | 11/2002 | Ueno et al. |
| 2002/0177778 A1 | 11/2002 | Averback et al. |
| 2002/0186478 A1 | 12/2002 | Watanabe et al. |
| 2003/0002036 A1 | 1/2003 | Haan et al. |
| 2003/0042493 A1 | 3/2003 | Kazakevich |
| 2003/0135092 A1 | 7/2003 | Cline et al. |
| 2003/0153811 A1 | 8/2003 | Muckner |
| 2003/0229270 A1 | 12/2003 | Suzuki et al. |
| 2004/0010183 A1 | 1/2004 | Dhindsa |
| 2004/0021859 A1 | 2/2004 | Cunningham |
| 2004/0037454 A1 | 2/2004 | Ozawa et al. |

(56) References Cited

U.S. PATENT DOCUMENTS

| | | |
|---|---|---|
| 2004/0046865 A1 | 3/2004 | Ueno et al. |
| 2004/0133073 A1* | 7/2004 | Berci et al. .................. 600/112 |
| 2004/0148141 A1 | 7/2004 | Tsujita et al. |
| 2004/0156124 A1 | 8/2004 | Okada |
| 2004/0218115 A1 | 11/2004 | Kawana et al. |
| 2005/0027166 A1 | 2/2005 | Matsumoto et al. |
| 2005/0096505 A1 | 5/2005 | Imaizumi et al. |
| 2005/0143627 A1 | 6/2005 | Cline et al. |
| 2005/0154319 A1 | 7/2005 | Cline et al. |
| 2005/0182291 A1 | 8/2005 | Hirata |
| 2005/0256373 A1 | 11/2005 | Bar-Or |
| 2006/0017913 A1 | 1/2006 | Kawamata et al. |
| 2006/0089554 A1 | 4/2006 | Ishihara et al. |
| 2006/0146322 A1 | 7/2006 | Komachi et al. |
| 2006/0211915 A1 | 9/2006 | Takeuchi et al. |
| 2006/0217594 A1 | 9/2006 | Ferguson |
| 2006/0241496 A1 | 10/2006 | Fengler et al. |
| 2008/0021274 A1 | 1/2008 | Bayer et al. |
| 2008/0027280 A1* | 1/2008 | Fengler et al. .................. 600/112 |
| 2009/0012361 A1 | 1/2009 | MacKinnon et al. |
| 2010/0125164 A1* | 5/2010 | LaBombard .................. 600/104 |
| 2010/0168588 A1 | 7/2010 | Matsumoto et al. |
| 2010/0198010 A1 | 8/2010 | Cline et al. |
| 2010/0277817 A1* | 11/2010 | Durell .................. 359/811 |
| 2014/0194687 A1 | 7/2014 | Fengler et al. |
| 2015/0230698 A1 | 8/2015 | Cline et al. |

FOREIGN PATENT DOCUMENTS

| | | |
|---|---|---|
| EP | 0 512 965 A1 | 11/1992 |
| EP | 0 672 379 A1 | 9/1995 |
| EP | 0 774 685 A2 | 5/1997 |
| EP | 0 774 865 A2 | 5/1997 |
| EP | 0 792 618 A1 | 9/1997 |
| EP | 1 374 755 A1 | 1/2004 |
| EP | 1 883 337 A1 | 2/2008 |
| EP | 2 051 603 A1 | 4/2009 |
| FR | 2 671 405 A1 | 7/1992 |
| JP | S-60-246733 A | 12/1985 |
| JP | S-61-159936 A | 7/1986 |
| JP | H-01-135349 A | 5/1989 |
| JP | 03-97439 A | 4/1991 |
| JP | 03-97441 A | 4/1991 |
| JP | 03-97442 A | 4/1991 |
| JP | 05-115435 A | 5/1993 |
| JP | 06-125911 A | 5/1994 |
| JP | H-07-155285 A | 6/1995 |
| JP | H-07-155286 A | 6/1995 |
| JP | H-07-155290 A | 6/1995 |
| JP | H-07-155291 A | 6/1995 |
| JP | H-07-155292 A | 6/1995 |
| JP | H-07-204156 A | 8/1995 |
| JP | H-07-222712 A | 8/1995 |
| JP | H-07-250804 A | 10/1995 |
| JP | H-07-250812 A | 10/1995 |
| JP | H-07-327913 A | 12/1995 |
| JP | H-08-126605 A | 5/1996 |
| JP | 08-140928 A | 6/1996 |
| JP | 08-140929 A | 6/1996 |
| JP | H-08-224208 A | 9/1996 |
| JP | H-08-224209 A | 9/1996 |
| JP | H-08-224210 A | 9/1996 |
| JP | H-08-224240 A | 9/1996 |
| JP | H-08-252218 A | 10/1996 |
| JP | 09-066023 A | 3/1997 |
| JP | 09-070384 A | 3/1997 |
| JP | H-10-127563 A | 5/1998 |
| JP | H-10-151104 A | 6/1998 |
| JP | 10-201707 A2 | 8/1998 |
| JP | 10-225427 A2 | 8/1998 |
| JP | H-10-201700 A | 8/1998 |
| JP | H-10-225426 A | 8/1998 |
| JP | H-10-243915 A | 9/1998 |
| JP | H-10-243920 A | 9/1998 |
| JP | H-10-308114 A | 11/1998 |
| JP | H-10-309281 A | 11/1998 |
| JP | H-10-309282 A | 11/1998 |
| JP | H-10-328129 A | 12/1998 |
| JP | 11-47079 A | 2/1999 |
| JP | 11-089789 A2 | 4/1999 |
| JP | H-11-104059 A | 4/1999 |
| JP | H-11-104060 A | 4/1999 |
| JP | H-11-104061 A | 4/1999 |
| JP | H-11-104070 A | 4/1999 |
| JP | H-11-113839 A | 4/1999 |
| JP | H-11-155812 A | 6/1999 |
| JP | H-11-244220 A | 9/1999 |
| JP | H-11-332819 A | 12/1999 |
| JP | 2000-504968 A | 4/2000 |
| JP | 2000-245693 A | 9/2000 |
| JP | 2000-354583 A | 12/2000 |
| JP | 2002-244122 A | 8/2002 |
| JP | 2004-024611 A | 1/2004 |
| JP | 2004-094043 A | 3/2004 |
| JP | 2004-163902 A | 6/2004 |
| JP | 2004-247156 A | 9/2004 |
| JP | 2004-292722 A | 10/2004 |
| JP | 2005-010315 A | 1/2005 |
| JP | 2005-058618 A2 | 3/2005 |
| JP | 2005-058619 A2 | 3/2005 |
| JP | 2005-058620 A2 | 3/2005 |
| JP | 2005-080819 A2 | 3/2005 |
| JP | 2005-081079 A2 | 3/2005 |
| JP | 2005-292404 A | 10/2005 |
| WO | WO-93/04648 A1 | 3/1993 |
| WO | WO-95/26673 A2 | 10/1995 |
| WO | WO-98/24360 A1 | 6/1998 |
| WO | WO-99/01749 A1 | 1/1999 |
| WO | WO-99/53832 A1 | 10/1999 |
| WO | WO-00/42910 A1 | 7/2000 |
| WO | WO-00/54652 A1 | 9/2000 |
| WO | WO-02/07587 A2 | 1/2002 |
| WO | WO-03/059159 A2 | 7/2003 |
| WO | WO-03/059159 A8 | 7/2003 |
| WO | WO-2006/116847 A1 | 11/2006 |
| WO | WO-2008/011722 A1 | 1/2008 |

OTHER PUBLICATIONS

Final Office Action mailed on May 11, 2011, for U.S. Appl. No. 11/412,715 (8 pages).
Final Office Action mailed on Jun. 18, 2015, for U.S. Appl. No. 14/154,177 (8 pages).
International Preliminary Report on Patentability mailed on Nov. 6, 2007, for International Application No. PCT/CA2006/000669 (9 pages).
International Preliminary Report on Patentability mailed on Feb. 3, 2009, for International Application No. PCT/CA2007/001335 (5 pages).
International Search Report mailed on Aug. 3, 2006, for International Application No. PCT/CA2006/000669 (3 pages).
International Search Report mailed on Dec. 7, 2007, for International Application No. PCT/CA2007/001335 (2 pages).
Non-Final Office Action mailed on Jan. 2, 2008, for U.S. Appl. No. 11/122,267 (5 pages).
Non-Final Office Action mailed on Dec. 10, 2010, for U.S. Appl. No. 11/412,715 (10 pages).
Non-Final Office Action with Restriction Requirement mailed on Mar. 4, 2011, for U.S. Appl. No. 11/830,323 (9 pages).
Non-Final Office Action mailed on Jun. 9, 2011, for U.S. Appl. No. 11/830,323 (5 pages).
Non-Final Office Action mailed on Dec. 14, 2011, for U.S. Appl. No. 11/412,715 (8 pages).
Non-Final Office Action mailed on Sep. 12, 2014, for U.S. Appl. No. 14/154,177 (4 pages).
Notice of Allowance mailed on Sep. 10, 2013, for U.S. Appl. No. 11/412,715 (8 pages).
Notice of Allowance mailed on Sep. 14, 2012, for U.S. Appl. No. 11/830,323 (8 pages).
Supplemental European Search Report mailed on Jan. 24, 2012, for European Patent Application No. 07785001.4 (6 pages).

(56) References Cited

OTHER PUBLICATIONS

Supplemental European Search Report mailed on Oct. 9, 2013, for European Patent Application No. 06721854.5 (6 pages).
Written Opinion of the International Searching Authority mailed on Aug. 3, 2006, for International Application No. PCT/CA2006/000669 (8 pages).
Written Opinion of the International Searching Authority mailed on Dec. 7, 2007, for International Application No. PCT/CA2007/001335 (4 pages).
Alfano, R.R. et al. (1987). "Fluorescence Spectra From Cancerous and Normal Human Breast and Lung Tissues," *IEEE Journal of Quantum Electronics* QE-23(10):1806-1811.
Andersson-Engels, S. et al. (1989). "Tissue Diagnostics Using Laser Induced Fluorescence," *Ber. Bunsenges Physical Chemistry* 93:335-342.
Bhunchet, E. et al. (2002). "Fluorescein Electronic Endoscopy: A Novel Method for Detection of Early Stage Gastric Cancer Not Evident to Routine Endoscopy," *Gastrointestinal Endoscopy* 55(4):562-571.
European Office Action mailed on Nov. 19, 2015, for EP Application No. 07 785 001.4, filed on Jul. 30, 2007, four pages.
Extended European Search Report mailed on Jan. 24, 2012 for EP Application No. 07 785 001.4, filed on Jul. 30, 2007, seven pages.
Final Office Action mailed on Nov. 24, 2009, for U.S. Appl. No. 11/009,965, fourteen pages.
Final Office Action mailed on Jun. 18, 2015, for U.S. Appl. No. 14/154,177, eight pages.
Final Office Action mailed on Jun. 5, 2014, for U.S. Appl. No. 12/761,462, fourteen pages.
Hung, J. et al. (1991). "Autofluorescence of Normal and Malignant Bronchial Tissue," *Lasers in Surgery and Medicine* 11:99-105.
International Search Report mailed on Jan. 21, 2002, for International Application No. PCT/US2001/022198, filed on Jul. 13, 2001, two pages.
Japanese Office Action mailed on Nov. 11, 2011, for Japanese Patent Application No. 2009-521077, filed on Jul. 30, 2007, four pages.
Japanese Office Action mailed on Feb. 17, 2012, for Japanese Patent Application No. 2008-509275, filed on Apr. 27, 2006, six pages.
Japanese Office Action mailed on Sep. 14, 2012, for Japanese Patent Application No. 2008-509275, filed on Apr. 27, 2006, seven pages.
Japanese Final Office Action mailed on Aug. 2, 2013, for Japanese Patent Application No. 2008-509275, filed on Apr. 27, 2006, four pages.
Japanese Office Action mailed on Sep. 19, 2014, for Japanese Patent Application No. 2013-246636, filed on Apr. 27, 2006, six pages.
Non-Final Office Action mailed on May 18, 2004, for U.S. Appl. No. 10/050,601, eight pages.
Non-Final Office Action mailed on Apr. 2, 2009, for U.S. Appl. No. 11/009,965, thirteen pages.
Non-Final Office Action mailed on Sep. 12, 2014, for U.S. Appl. No. 14/154,177, four pages.
Non-Final Office Action mailed on Jun. 20, 2008, for U.S. Appl. No. 11/009,398, fifteen pages.
Non-Final Office Action mailed on Jan. 2, 2008, for U.S. Appl. No. 11/122,267, five pages.
Non-Final Office Action mailed on Dec. 10, 2010, for U.S. Appl. No. 11,412,715, ten pages.
Non-Final Office Action mailed on Dec. 14, 2011, for U.S. Appl. No. 11,412,715, eight pages.
Non-Final Office Action mailed on Jun. 1, 2007, for U.S. Appl. No. 10/899,648, seven pages.
Non-Final Office Action mailed on Nov. 23, 2009, for U.S. Appl. No. 11/969,974, seven pages.
Non-Final Office Action mailed on Aug. 16, 2013, for U.S. Appl. No. 12/761,462, ten pages.
Non-Final Office Action mailed on Aug. 16, 2013, for U.S. Appl. No. 12/761,523, nine pages.
Non-Final Office Action mailed on Jul. 17, 2003, for U.S. Appl. No. 09/905,642, six pages.
Non-Final Office Action mailed on Jan. 20, 2016, for U.S. Appl. No. 14/629,473, fourteen pages.
Notice of Allowance mailed on Mar. 10, 2005, for U.S. Appl. No. 10/050,601, five pages.
Notice of Allowance mailed on Aug. 26, 2004, for U.S. Appl. No. 10/050,601, eight pages.
Notice of Allowance mailed on Oct. 5, 2007, for U.S. Appl. No. 10/899,648, six pages.
Notice of Allowance mailed on Jan. 2, 2008, for U.S. Appl. No. 10/899,648, three pages.
Notice of Allowance mailed on Feb. 25, 2010, for U.S. Appl. No. 11/969,974, four pages.
Notice of Allowance mailed on Oct. 10, 2014, for U.S. Appl. No. 12/761,462, ten pages.
Notice of Allowance mailed on Apr. 7, 2004, for U.S. Appl. No. 09/905,642, six pages.

\* cited by examiner

Single Use Optical Filter Installation

SYSTEM AND METHOD FOR DEPOSITION AND REMOVAL OF AN OPTICAL ELEMENT ON AN ENDOSCOPE OBJECTIVE

CROSS-REFERENCE TO RELATED APPLICATIONS

This application is a divisional of co-pending U.S. application Ser. No. 11/830,323, filed Jul. 30, 2007, which claims the benefit of U.S. Provisional Application No. 60/833,897, filed Jul. 28, 2006, the entire content is incorporated herein by reference.

FIELD OF THE INVENTION

The invention relates to medical imaging systems and more particularly, to a video endoscope capable of operating in multiple imaging modes to acquire color or multi-channel fluorescence and reflectance images.

BACKGROUND OF THE INVENTION

Fluorescence endoscopy utilizes differences in the fluorescence response of normal tissue and tissue suspicious for early cancer as a tool in the detection and localization of such cancer. The fluorescing compounds or fluorophores that are excited during fluorescence endoscopy may be exogenously applied photo-active drugs that accumulate preferentially in suspicious tissues, or they may be the endogenous fluorophores that are present in all tissue. In the latter case, the fluorescence from the tissue is typically referred to as autofluorescence or native fluorescence. Tissue autofluorescence is typically due to fluorophores with absorption bands in the UV and blue portion of the visible spectrum and emission bands in the green to red portions of the visible spectrum. In tissue suspicious for early cancer, the green portion of the autofluorescence spectrum is significantly suppressed. Fluorescence endoscopy that is based on tissue autofluorescence utilizes this spectral difference to distinguish normal from suspicious tissue.

A fluorescence endoscopy video system typically includes an endoscopic light source that is capable of operating in multiple modes to produce white light, reflectance light, fluorescence excitation light, or fluorescence excitation light with reference reflectance light, depending on particular filters inserted between the light source and the illuminated tissue, and between the tissue and the imaging sensor, respectively. A compact camera with the imaging sensor, such as a color CCD imager, can be disposed in the insertion portion (distal end or tip) of the endoscope; alternatively, the camera can be placed at the proximal end of the endoscope, in which case the acquired image can be transmitted from the distal end of the endoscope to the proximal end through a light guide.

Commonly assigned US Patent Application Serial No. 2006/0241496 A1 discloses a distal filter that can be placed over the distal end of a conventional white light imaging endoscope to allow the endoscope to perform fluorescence and white light examinations of a patient. The primary function of this filter is to prevent the transmission of blue light illumination used for fluorescence excitation and to transmit all other visible light over the field of view of the endoscope objective lens.

The filter may be mounted in a frame that is snap-fitted over the distal end face of an endoscope. The filter and/or frame may be secured to the endoscope with a mechanical, adhesive, magnetic force or other means.

Since fitting of the filter is performed in a clinical environment and for medical purposes, such fitting must be simple, accurate and reliable. In that regard, the small size of the filter represents a handling challenge. Even more challenging is the accuracy required for placing the filter over the video endoscope objective lens with sufficient precision. The tips of video endoscopes are typically 5-13 mm across and may include multiple closely spaced illumination ports, water ports, and one or more additional working channels, all sharing space with the objective lens.

Therefore, there is a need for a system and a method which enables accurate and reliable placement of an optical element, such as a filter, over the video endoscope objective lens in a clinical environment.

BRIEF SUMMARY OF THE INVENTION

The invention is directed to an applicator for precisely and reliably placing and attaching an optical element to the distal end of an endoscope in a clinical setting.

According to one aspect of the invention, an applicator for attaching an optical element to an optical port disposed on a distal end of an endoscope includes a base having an opening, with the optical element releasably supported in the opening, one or more alignment members extending from the proximal side of the base, and an actuatable element disposed on the distal side of the base and adapted to transmit a force to the optical element, wherein the optical element is released in a proximal direction by actuating the force-transmitting element.

According to another aspect of the invention, an applicator is provided that is adapted to engage with a distal end of an endoscope, wherein the distal end includes a registration feature. The applicator includes a base having at least one alignment member that is configured to engage with the registration feature of the endoscope's distal end, and an optical element releasably disposed in or on an opening of the base and in alignment with an optical port in the endoscope's distal end when the at least one alignment member engages with the registration feature of the endoscope's distal end. The applicator further includes an actuator disposed on or in the base and configured to release the optical element from the base and to urge the optical element in a proximal direction under an external force applied to the actuator.

According to yet another aspect of the invention, in a method for attaching an optical element to an optical port disposed on a distal end of an endoscope with one or more registration features, an applicator is provided which releasably holds the optical element, which has an adhesive side facing the endoscope's distal end and an opposing non-adhesive side. The applicator comprises one or more alignment members. The method further includes the steps of engaging one or more of the alignment members disposed on the applicator with corresponding ones of the registration features disposed at the endoscope's distal end, thereby aligning the optical element with the optical port, and applying with the applicator an external force against the non-adhesive side of the optical element so as to disengage the optical element from the applicator and urge the adhesive side of the optical element into contact with the optical port.

The invention is also directed to a kit for converting a white-light endoscope to an endoscope for combined white-light/fluorescence imaging. The kit includes the afore-described applicator in a sterile package and one or more cleaning implements as well as a removal tool to remove the optical element from the optical port at the distal end of the endoscope after use. The kit may further include a cleaning solution that may be impregnated on or in the cleaning implement, or that may be available for such impregnation by the user.

Embodiments of the invention may include one or more of the following features. The actuatable element may be implemented as a piston slideably disposed in a piston housing that extends from the distal side of the base, with the piston adapted to transmit the force to the optical element. The actuatable element may also be configured as a lever arm or a membrane; a compliant tip made, for example, of silicone rubber, may be interposed between an end of the piston, lever arm or membrane facing the first major surface of the optical element and the optical element.

The one or more alignment members may be integrally formed with the base and configured to engage with a corresponding registration feature disposed on the distal end of the endoscope, which may be ports other than the optical port, or other structural surface features formed on the endoscope's distal end. Advantageously, the base may also include one or more gripping surfaces for handling the applicator.

The optical element may be an optical filter fabricated, for example, of polycarbonate. The optical element may have a first major surface that is non-adhesive and a second major surface of the optical element facing the optical port (when the endoscope and applicator are registered) that is adhesive for attachment to, for example, an imaging lens. The adhesive side of the optical element may supported on a shoulder or recess extending radially inward in the opening; alternatively, the adhesive side of the optical element may supported by a metal disk which is disposed on the base and includes the opening for the optical element. In certain embodiments, the invention provides an endoscope with one of the applicators described herein.

Further features and advantages of the present invention will be apparent from the following description of preferred embodiments and from the claims.

BRIEF DESCRIPTION OF THE DRAWINGS

The following figures depict certain illustrative embodiments of the invention in which like reference numerals refer to like elements. These depicted embodiments are to be understood as illustrative of the invention and not as limiting in any way.

DETAILED DESCRIPTION OF THE INVENTION

Figure 1A:
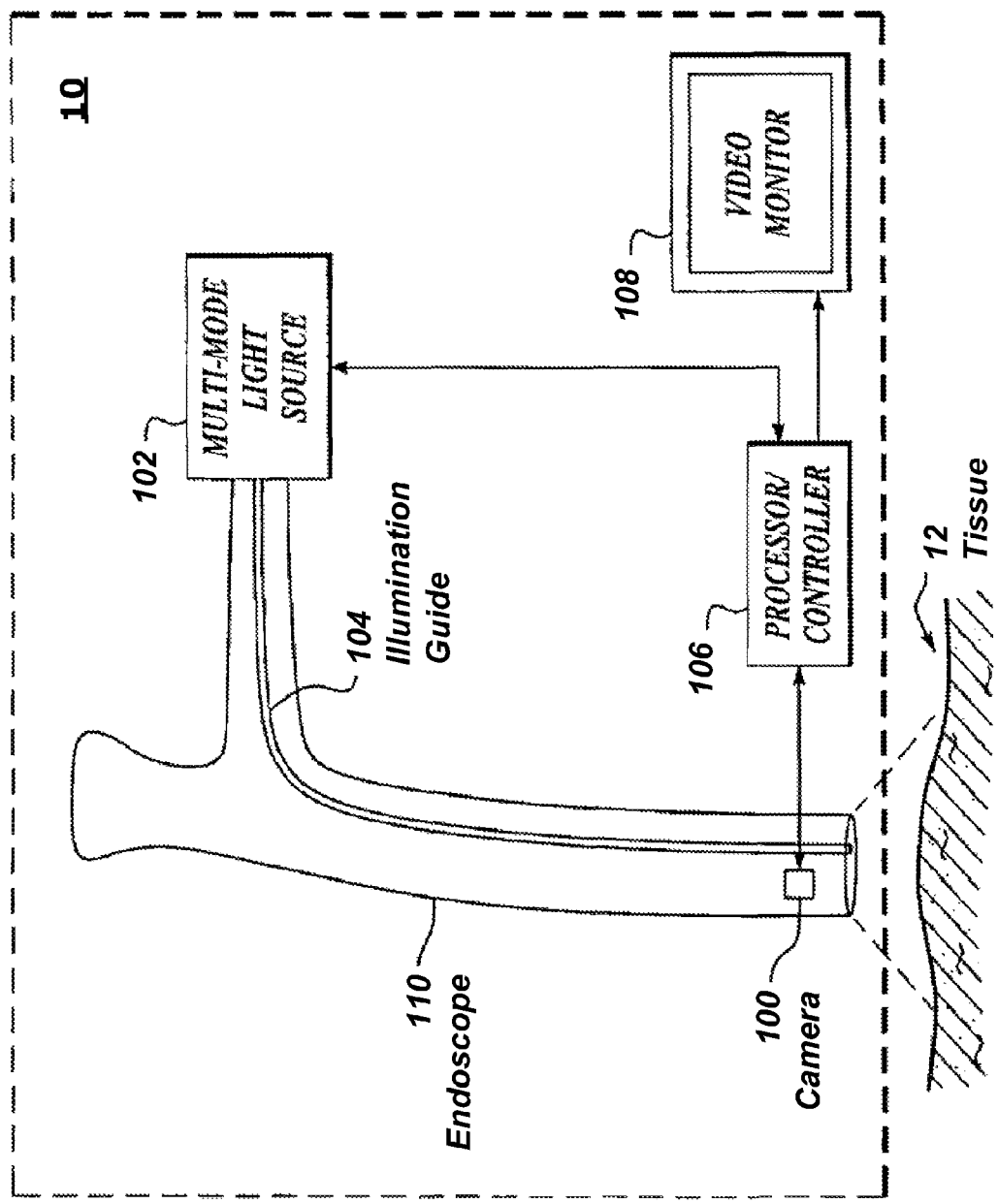
FIG. 1A is a block diagram of a fluorescence endoscopy video system in accordance with one embodiment of the present invention.

FIG. 1A is a block diagram of an exemplary fluorescence endoscopy video system 10 which includes a multi-mode light source 102 that generates light for obtaining color and fluorescence images. The use of light source 102 for obtaining different types of images will be described in further detail below. Light from the light source 102 is supplied to an illumination guide 104 of an endoscope 110, which then illuminates a tissue sample 12 to be imaged.

As shown in FIG. 1A, the system also includes a camera 100, such as a color CCD camera, in particular a color CCD camera capable of operating under low light conditions, located at the insertion end, also referred to as distal end or tip, of the endoscope 110. The light from the tissue 12 is captured by the camera 100. With the camera 100 located at the insertion end of the endoscope, the resulting endoscope 110 can be characterized as a fluorescence video endoscope, similar to video endoscopes currently on the market (such as the Olympus CF-240L) in utility. In addition to conventional color imaging, the endoscope can be utilized for fluorescence/reflectance and/or fluorescence/fluorescence imaging. Locating the camera at the insertion end of the endoscope improves the light sensitivity and image resolution compared to endoscopes having an imaging guide or a relay lens.

A processor/controller 106 communicates with the camera 100 and the light source 102 via electrical and/or optical signal transmission lines routed within the endoscope, and produces video signals that can be displayed on a video monitor 108. Alternatively, the camera 100 can communicate with the processor/controller 106 over a wireless link (not shown).

Figure 1B:
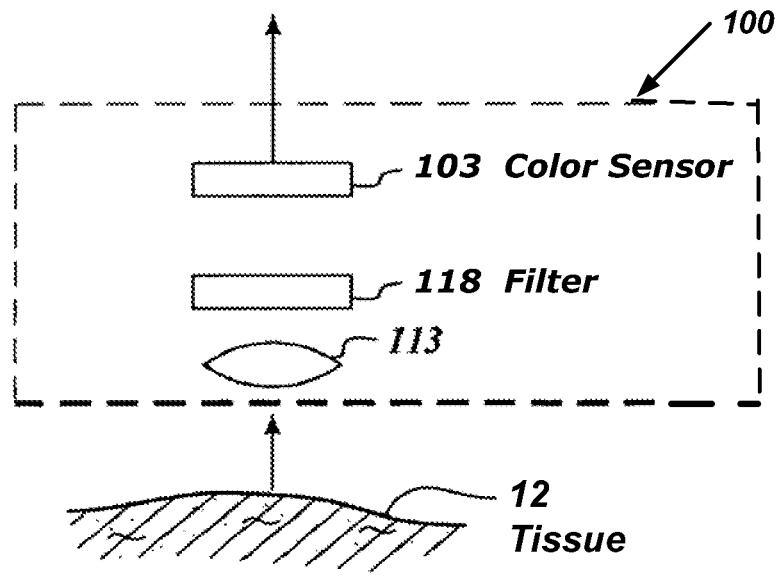
FIG. 1B shows the distal end of the fluorescence endoscopy video system of FIG. 1A with a filter incorporated inside the camera.

As shown in FIG. 1B, the exemplary camera 100 includes a single color CCD sensor 103 and suitable imaging optics 113. Each of the pixel elements on the single color CCD sensor 103 is covered by an integrated filter, typically red, green or blue. These filters define the wavelength bands of fluorescence and reflectance light that reach the individual pixel elements. Such filters typically have considerable spectral overlap between the red, green, and blue passbands, which can lead to considerable crosstalk when imaging low-intensity fluorescence light in the presence of the much more intense reflected excitation light. It is therefore advantageous to place a separate filter 118 in the optical path before the CCD sensor 103 which passes the fluorescence light, but reduces the intensity of reflected excitation light to the same level as that of the fluorescence light. The individual primary fluorescence and reference image signals can be generated from the image signals received by processor/controller 106 from CCD sensor 103. It will be understood that instead of a single color CCD sensor, the color image sensor 103 may be a three-CCD color image sensor assembly, a color CMOS image sensor, or a three-CMOS color image sensor assembly, optionally with charge carrier multiplication.

Figure 1C:
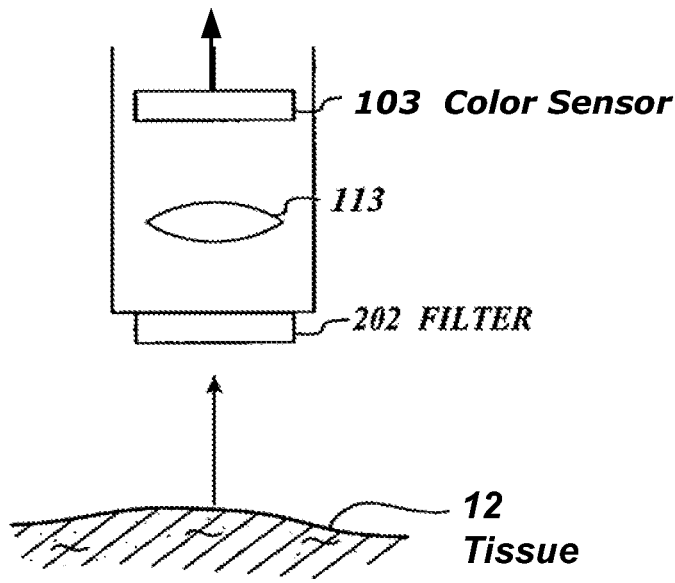
FIG. 1C shows the distal end of the fluorescence endoscopy video system of FIG. 1A with an external distal filter that allows a conventional endoscope to perform both fluorescence and white light imaging.

As also shown in FIG. 1B, the filter 118 in current fluorescence video-endoscopy systems is typically built in to the endoscope's distal end (typically between the objective lens and the low light image sensor), thus requiring dedicated endoscopes. Filter 118 blocks the strong excitation light used to excite the tissue fluorescence these systems are intended to image. This built-in filter distinguishes these endoscopes from those used for conventional video-endoscopy. To be able to use a conventional video-endoscope, which lacks the built-in filter 118, for also imaging tissue fluorescence, an externally mounted filter 202 can instead be applied externally to a conventional video-endoscope that contains a sufficiently sensitive image sensor to also image tissue fluorescence, as shown in FIG. 1C. This combination of a conventional video endoscope and an externally mounted filter 202 can be used in conjunction with an appropriate endoscopy light source 102 to image both in both color (or white light) and fluorescence modes.

FIG. 1C illustrates one embodiment of a conventional video-endoscope with a distal filter 202 placed over the distal end or tip to allow the endoscope to perform fluorescence and white light examinations of a patient. As will be described below, the filter 202 blocks excess excitation light from reaching the image sensor 103, but allows sufficient blue light intensity to pass in order to render white light images with proper white balance.

Figure 2A:
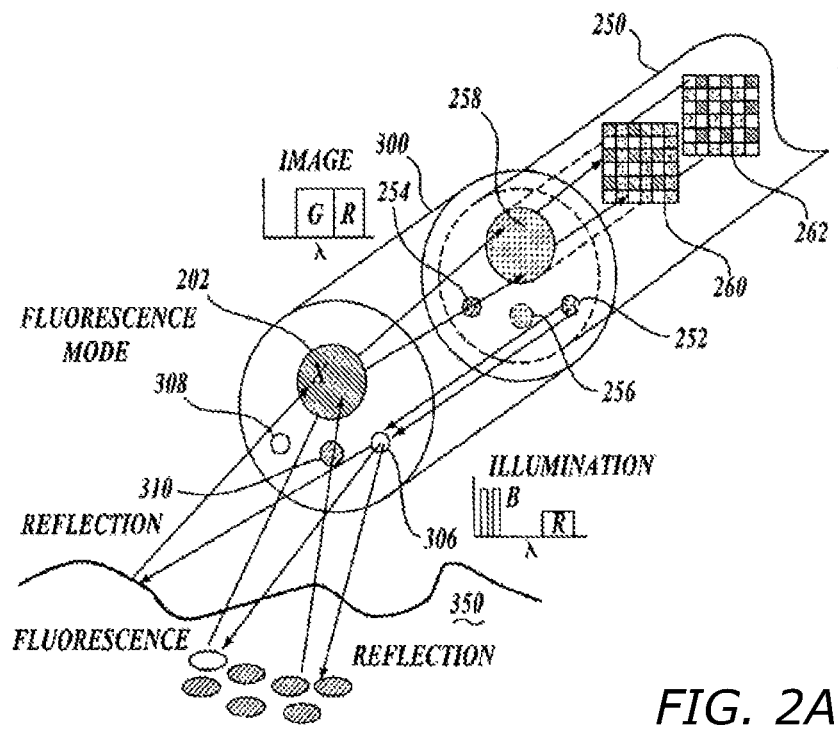
FIGS. 2A and 2B show operation of the distal filter of FIG. 1B for fluorescence (FIG. 2A) and white light mode imaging (FIG. 2B)
Figure 2B:
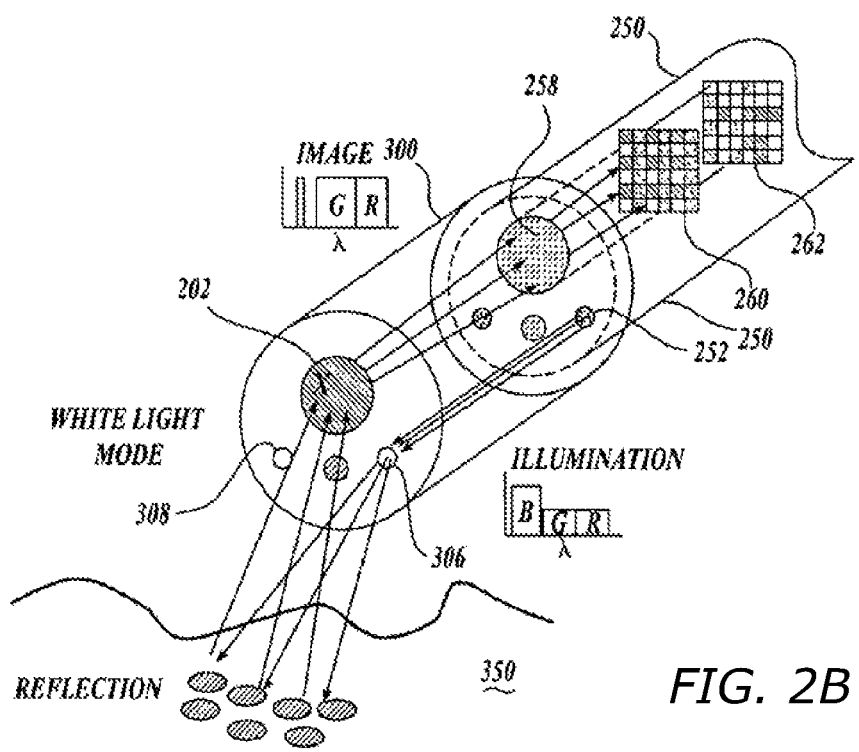

FIGS. 2A and 2B illustrate the operation of the distal filter 202 in further detail. An exemplary endoscope 250 includes illumination ports 252, 254 that supply illumination light to an area of interest. Another port 256 is the distal entrance to a working channel through which endoscopy tools can be passed in order to perform a desired task such as obtaining a biopsy sample, marking tissue with dye or perform some other diagnostic or therapeutic procedures. Light that is reflected from the tissue 350 is captured by a lens 258 that images the light onto a color sensor 262. In this embodiment, the color light sensor is a CCD, CMOS or equivalent image sensor 262 with a mosaic filter 260, such as a RGB filter, positioned in front of sensor 262. Image signals produced by the image sensor are transmitted to image processor 106 (FIG. 1A) that converts the signals into video signals that can be displayed on monitor 108, transmitted to another location, for example, for remote diagnosis, or recorded on a storage medium for later review or comparison.

The endoscope 250 is shown as being fitted with the distal end filter 202. As will be described in more detail below, the filter 202 is designed as a single-use device that is applied to the tip of the conventional color CCD video endoscope prior to endoscopy and that is removed following endoscopy. The filter covers the field of view of the video endoscope objective lens 258, but does not block the illumination ports 252, 254 or working channel 256, water ports (not shown) or other features that may be located on the endoscope tip. The filter remains firmly attached to the endoscope tip, preferably directly to lens 258, until it is deliberately removed.

The filter 202 is positioned in front of the imaging lens 258 and prevents excitation light from reaching the image sensor. In one embodiment, the filter removes the excitation light having wavelengths in the UV/blue spectral range, for example a wavelength range between about 370 nm and about 450 nm, or some subset of this wavelength range, but passes some blue light, for example 451-480 nm, for use in white light imaging, as will be described below. Because most endoscopes have objective lenses with a wide field of view, the filter should block excitation light over a correspondingly wide field of view. The filter should also be thin enough so as not to introduce optical aberrations or interfere with the mechanical properties and maneuverability of the endoscope tip. Examples of suitable filters are, for example, dye-based absorption filters designed to block the desired range of excitation light and to operate over a wide field of view, such as Kodak Wratten gel filters.

As shown in FIG. 2A, the distal filter 202 allows fluorescence images to be obtained in at least two modes. In a first mode, excitation light, typically in the UV/blue wavelength spectral band, is provided from a light source (not shown) and through the illumination ports 252, 254 whereupon it is incident on a tissue sample 350. A portion of the excitation light causes the tissue sample to produce fluorescence light while another portion of the excitation light is reflected off the surface of the tissue 350. Excitation light reflected from the surface of the tissue 350 is blocked by the filter 202, whereas the fluorescence light and light in other spectral bands passes through filter 202.

In one fluorescence imaging mode, only fluorescence light is used to produce video images of the tissue. In another mode, the tissue is illuminated with the excitation light and some amount of reflectance light. As shown in the exemplary embodiment depicted in FIG. 2A, the reflectance light is in the red spectral band. The reflectance light passes through filter 202 and the mosaic filter 260 disposed in front of image sensor 262. Images of the tissue are obtained by combining, for example, the green pixels from image sensor 262 to obtain a fluorescence image in the green spectral band and the red pixels from image sensor 262 to obtain a reflectance image in the red spectral band. Alternatively, the reflectance light may be provided in the green spectral band and a fluorescence image in the red spectral band. In yet another embodiment, the reflectance image can be produced from blue reflectance light having wavelengths that are not filtered by filter 202. The fluorescence and reflectance images may be combined and displayed on video monitor 108 (FIG. 1A). To prevent the intense light from the reflectance image from overpowering the low light level of the fluorescence image, the amount of reflectance light supplied from the light source is selected to be comparable to the amount of fluorescence light received by image sensor 262.

As shown in FIG. 2B, endoscope 250 can also be used to obtain white light images of the tissue 350 by illuminating the tissue with light having red, green and blue spectral components. The illumination light is reflected by the tissue sample 350, passes through filter 202 and is focused onto image sensor 262 by the endoscope's imaging lens 258. Because the filter 202 removes most of the blue reflectance light, the light received by image sensor 262 includes excess red and green light. To compensate for the reduced blue light intensity at the image sensor, the illumination light should either contain excess blue light intensity in the band that passes through the filter 202 or contain reduced green and red light intensity so that the resulting image produced by the image sensor may be white balanced. Additional fine-tuning of the white balance of the images produced by the image sensor 262 can be accomplished by image processing software in the image processor 106 (FIG. 1A).

Figure 3:
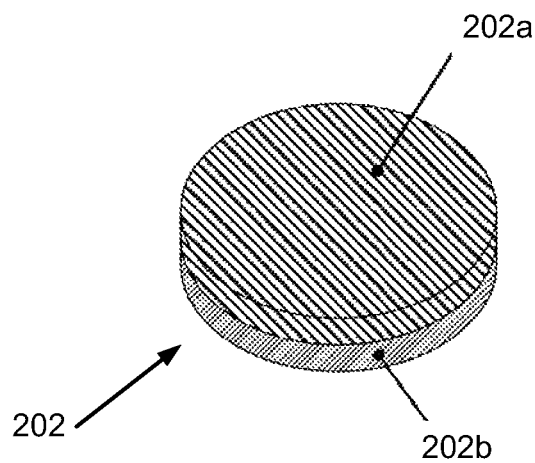
FIG. 3 shows schematically an exemplary embodiment of a distal filter according to the invention.

The filter 202 may be secured to the endoscope's distal end with an adhesive. In one embodiment, illustrated in FIG. 3, filter 202 may be composed of various flexible, optically transparent materials, such as a dyed polycarbonate filter disk 202a with a diameter of several millimeters. The filter disk 202a may be laminated to an optically clear adhesive 202b for a total thickness of approximately 100 μm.

Since the filter is applied externally to the endoscope's distal end in a clinical environment and for medical purposes, the attachment must be reliable, simple, accurate and free of contaminants. In that regard, the small size of the filter represents a handling challenge. Endoscopy suites are not equipped with tools for such purposes, medical staff is frequently gloved and pre-endoscopy preparation time is often limited. Even more challenging is the accuracy required for placing the filter over the video endoscope objective lens with sufficient precision. The tips of video endoscopes 60 are typically 5-13 mm across and can be very crowded with multiple illumination ports 252, 254, water ports, and one or more working channels 256, all sharing space with the objective lens 258. (See FIGS. 2A and 2B and FIG. 4).

Mechanical considerations are not the only concern in fitting a filter to an endoscope objective. Endoscope objectives have a wide field of view (typically between about 120° and about 170°) and the optical aperture of the filter should not occlude any part of that field. Moreover, trapping of contaminants or air between the filter and the objective lens which could degrade the optical performance of the video endoscope should also be prevented or at least minimized. Although endoscopes are typically cleaned, washed and disinfected by specialized washing machines, it is not uncommon for some form of residue to remain on the objective lens. Such residue needs to be cleaned prior to endoscopy and in the case where a filter is to be fitted to the objective lens, such cleaning would need to take place prior to fitting the filter. Any remaining contaminants between the filter and the objective may also adversely affect the adhesion of the filter to the endoscope objective. Once fitted, the filter needs to remain firmly and securely attached throughout the endoscopy procedure. Finally, since the filter will contact mucous membranes, it is desirable that the filter itself should be sterile and remain so until the endoscope is inserted into the patient at the beginning of the procedure.

Figure 4:
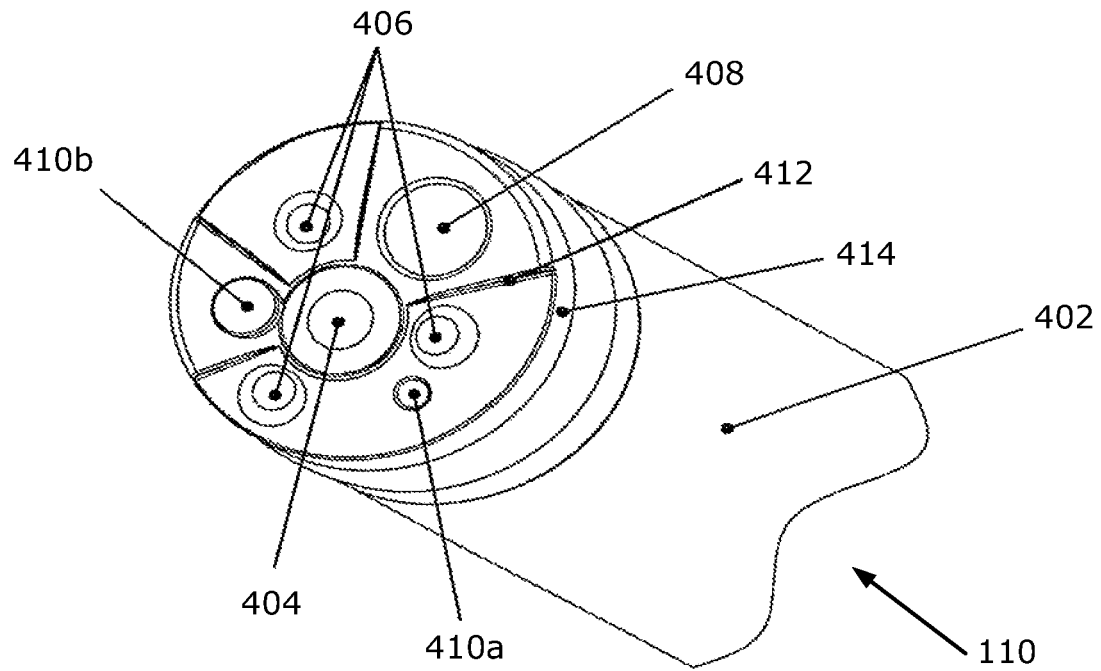
FIG. 4 shows an exemplary configuration of a distal end of an endoscope with optical and working ports.

FIG. 4 shows in a perspective view another exemplary configuration of the distal end 402 of an endoscope 110 with an optical port 404, illumination ports 406, working port 408, water ports 410a, 410b and other features, such as tip surface contours 412, which may aid in placing filter 202 on the endoscope's distal end 402.

Figure 5:
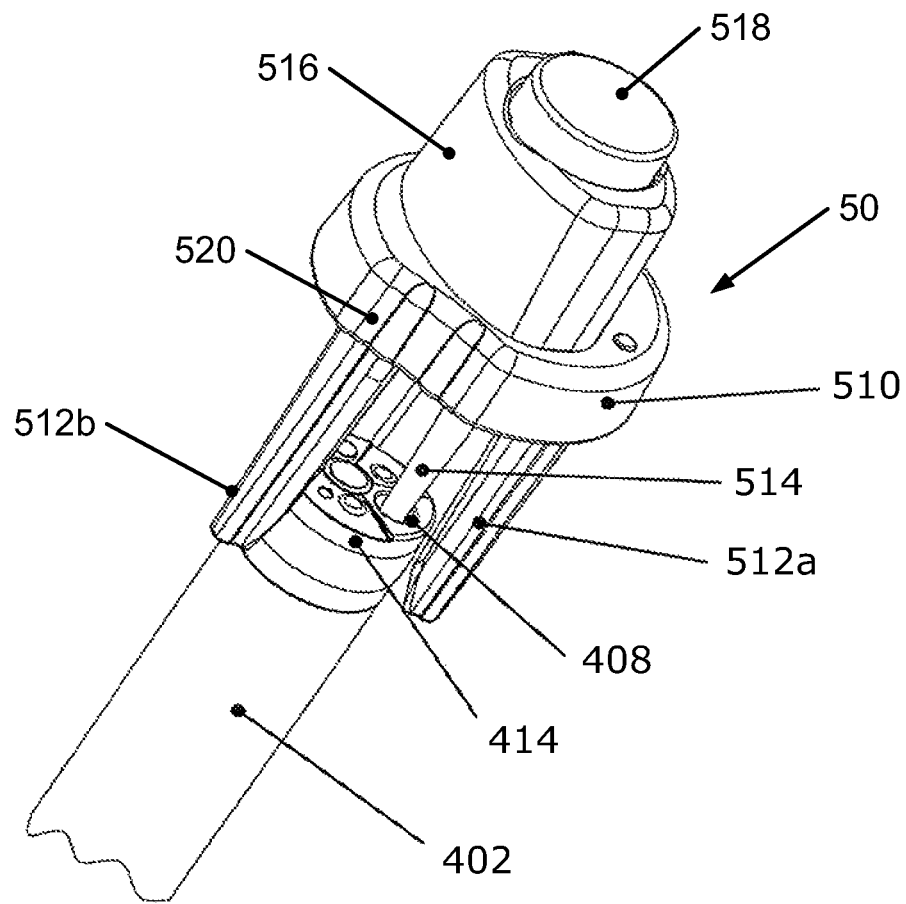
FIG. 5 shows an embodiment of an applicator according to the invention placed over the distal end of an endoscope.
Figure 6:
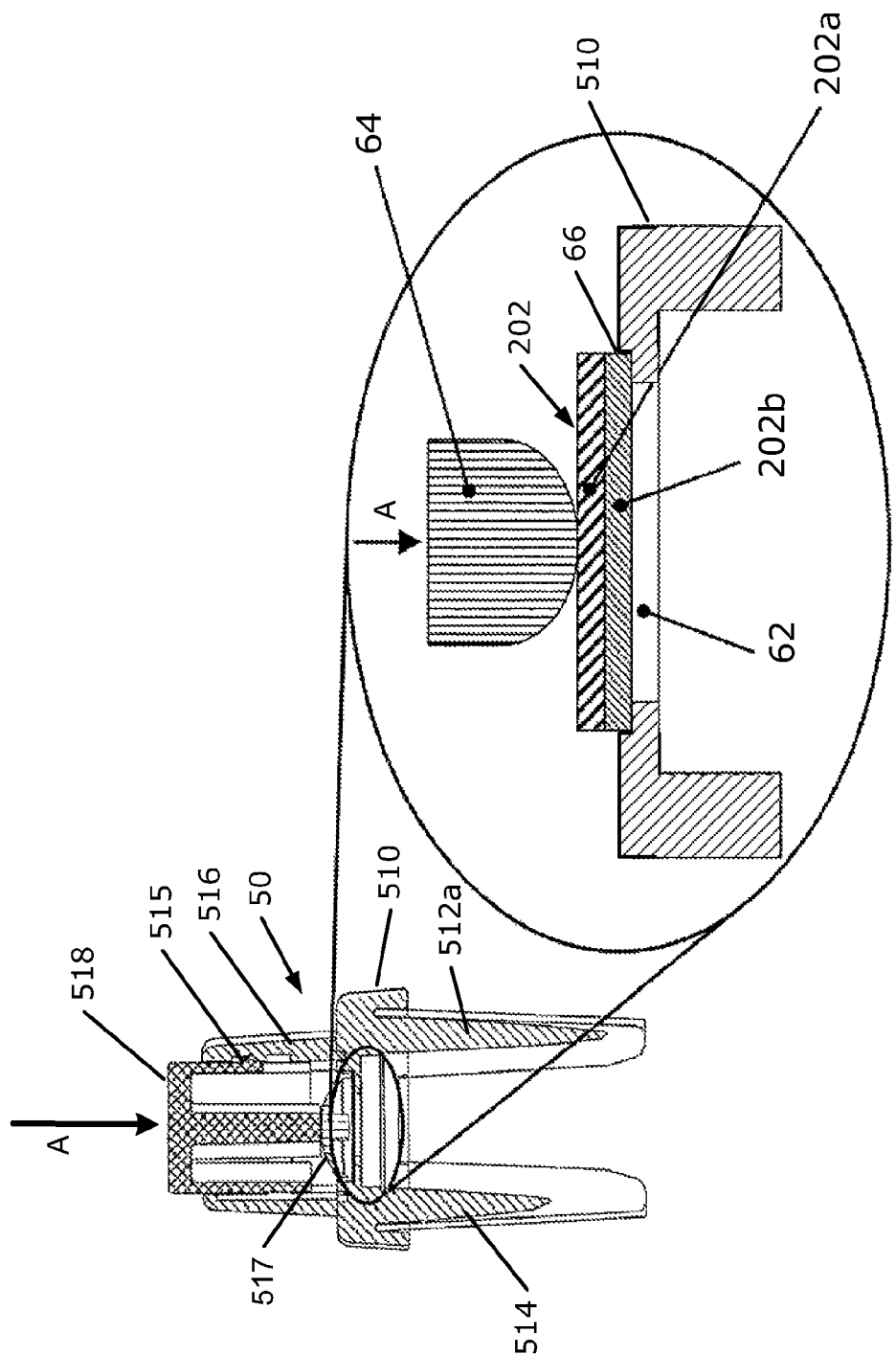
FIG. 6 shows the applicator of FIG. 5 in a cross-sectional view and as an inset, at an enlarged scale, the support for the distal filter and a piston for urging the filter against the optical port.
Figure 6A:
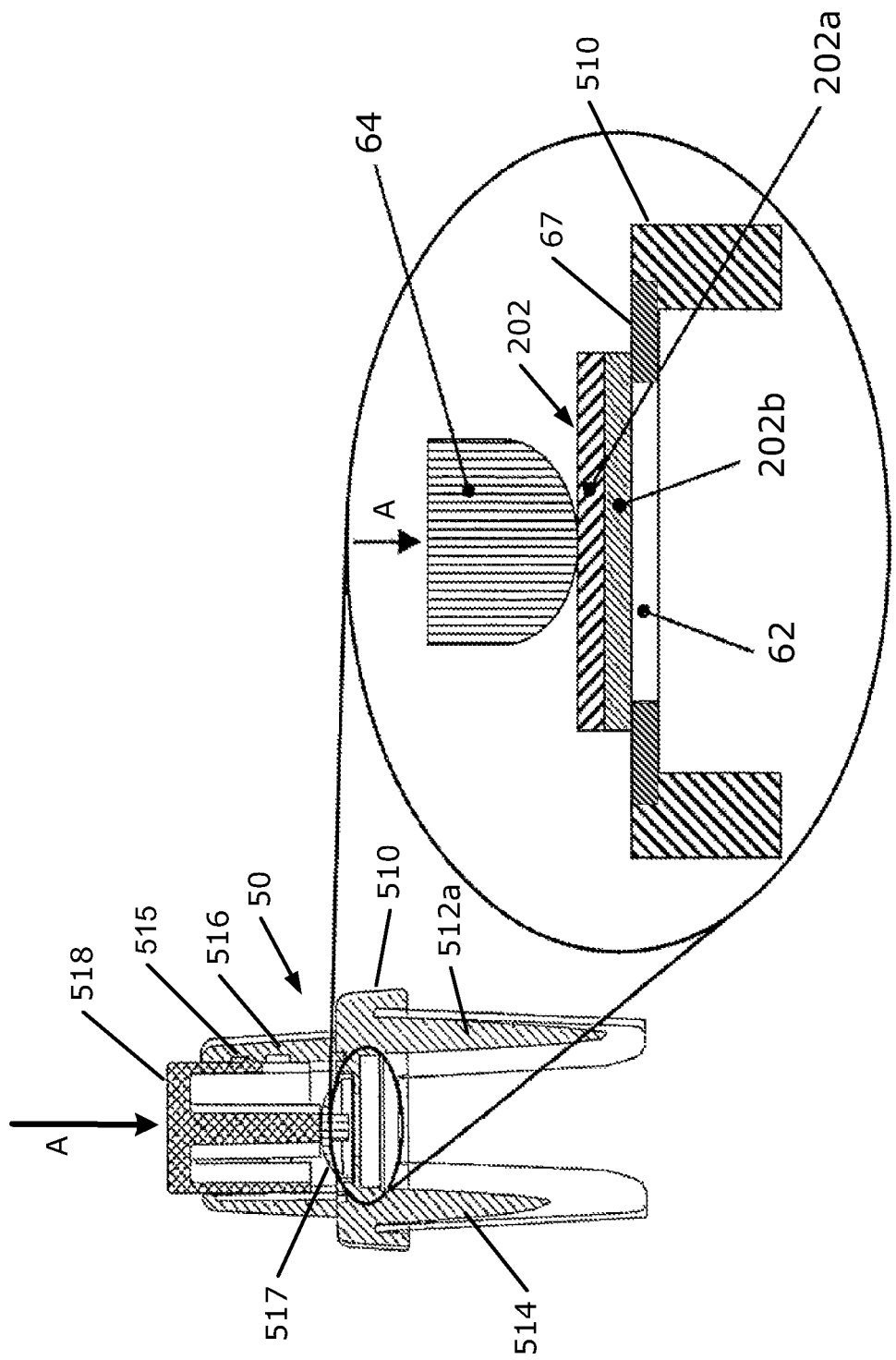
FIG. 6A shows another embodiment of the support for the distal filter.
Figure 6B:
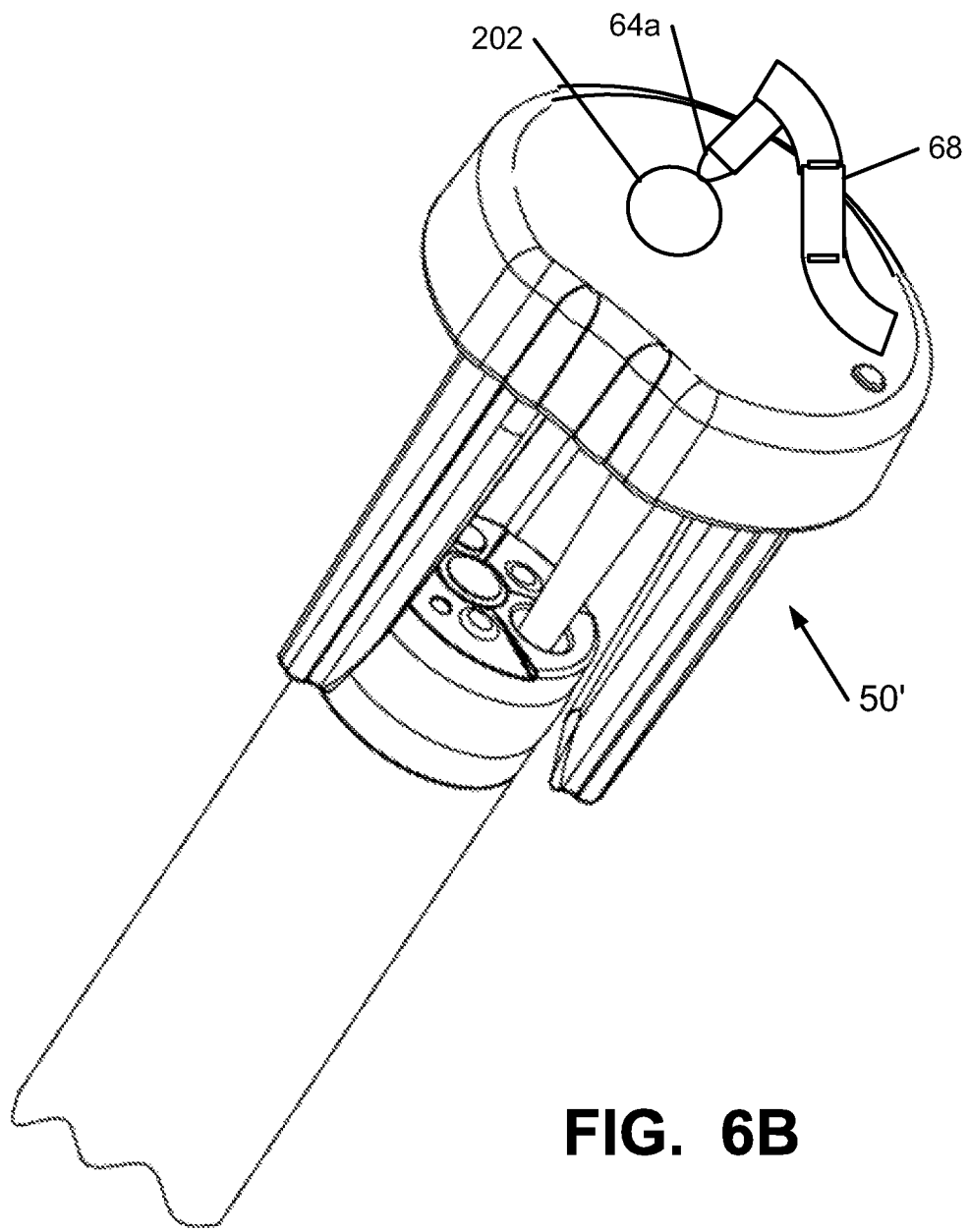
FIG. 6B shows another embodiment of an applicator according to the invention placed over the distal end of an endoscope.

FIG. 5 and FIGS. 6 through 6B show an applicator 50 according to the invention. Applicator 50, when properly registered with endoscope's distal end 402, can be used to accurately place filter 202 (or any other optical element such as a lens adapter or relay optics) on optical port 404 of distal end 402. Applicator 50 is supplied with filter 202 already mounted therein, as described below in more detail with reference to FIG. 6. The exemplary embodiment of applicator 50 illustrated in FIG. 5 has a substantially round base section 510 with gripping surface(s) 520 to aid an operator in handling the applicator 50. The distal end of base section 510 (i.e., the end pointing away from distal end 402) transitions into or is attached, for example by a snap-in connection, to a longitudinally extending, substantially cylindrical projection 516 adapted to receive a piston 518 which is movable in the longitudinal direction, as indicated by arrow A in FIG. 6. Alignment members, such as projections 512a, 512b, 514, are integrally formed on, such as molded, or attached to the proximal end of base section 510. The exemplary projection 514 is adapted to engage with, for example, the working channel 408, whereas the projections are adapted to engage with a circumferential shoulder 414 of endoscope distal end 402 to position adapter 50 on distal end 402 with the proper orientation. Other embodiments may use other locating features, such as the water ports 410a, 410b and tip surface contours 412.

As suggested in FIGS. 6 and 6A, the piston 518 may be held in place by a small detent 515 located, for example, near the top of the piston housing. Detent 515 prevents the piston 518 from being inadvertently activated and prematurely ejecting the filter before a force is intentionally applied to the piston to place the optical element 202 on optical port 404.

FIG. 6 shows applicator 50 in cross-section, with the insert showing the placement of filter 202 on base section 510 in more detail. Base section 510 has an opening 62 which optionally includes an annular inward recess or shoulder 66. The diameter of opening 62 is preferably slightly smaller than the diameter of filter 202, thereby precisely and securely supporting filter 202 in opening 62. When the applicator 50 is properly positioned over the distal end 402 of the endoscope, the projections 512a, 512b, 514 place the opening 62 directly over the optical port or objective lens 404 of the endoscope. The filter 202 is then centered in the opening 62 with the adhesive side 202b of filter 202 facing the optical port 404.

In an alternative embodiment illustrated in FIG. 6A, the top of the base may be provided with a metal disk 67 having a hole that will be precisely positioned by the applicator 50 over the endoscope's optical port 404. The hole in the disk is slightly smaller in diameter than the optical element that is centered over the hole. The disk 67 may be made, for example, of a thin brass sheet or another material capable of holding the optical element before its release by the force applied to the piston.

In the exemplary embodiment depicted in FIGS. 6 and 6A, a membrane 517 covers substantially the entire opening in base 510. A compliant tip 64, 64a is formed in the center of the membrane 517 on the side facing the optical element 202. The tip 64, 64a presses against the center of optical element 202 when an external force is applied to piston 518 in the direction of arrow A. In this way, the optical element is pressed against the optical port 404 (or a lens in the optical port) from the center of the lens outwardly, thereby eliminating trapped air bubbles. Alternatively, the tip may be disposed on the end of the piston facing the optical element without an interposed membrane.

Figure 6C:
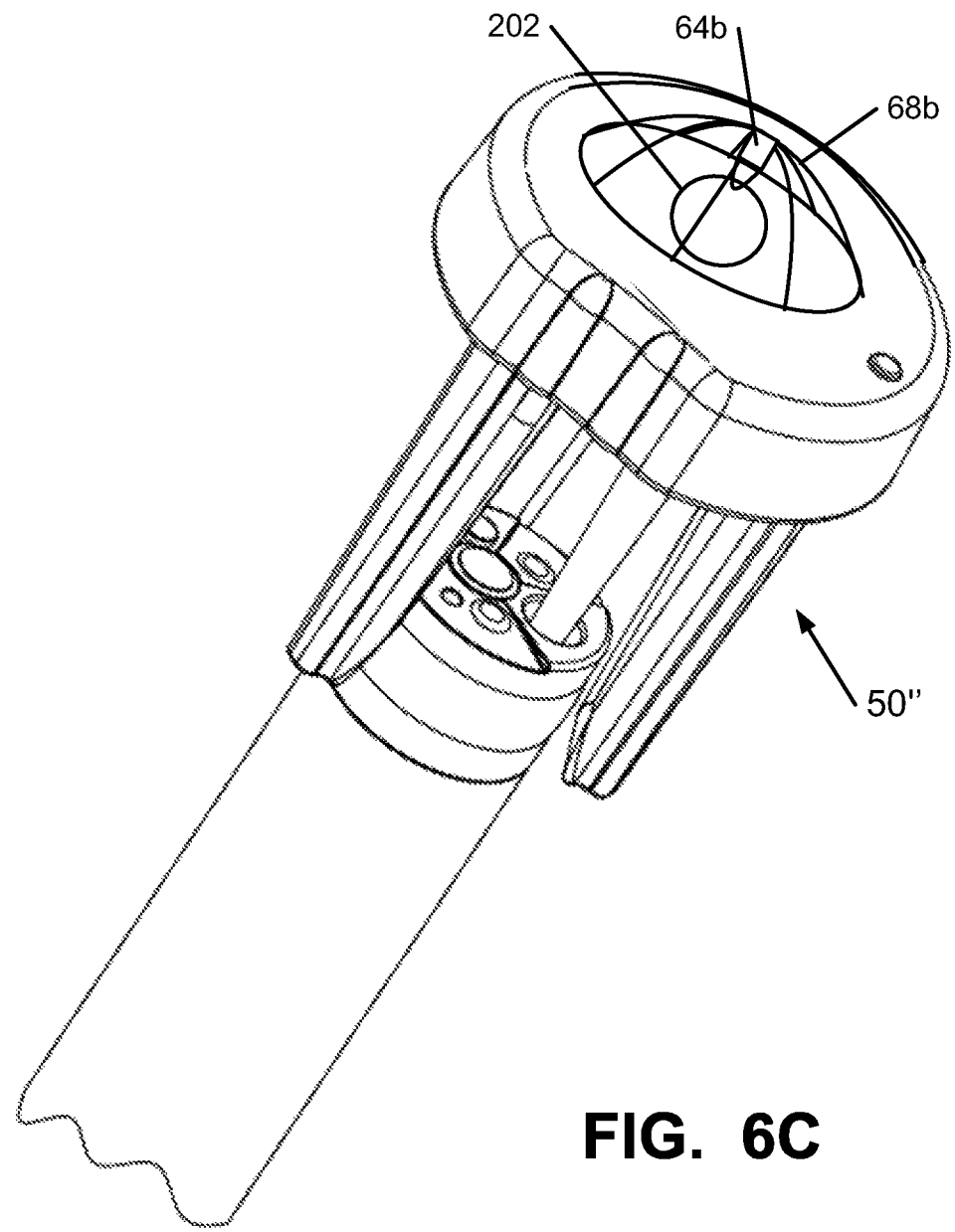
FIG. 6C shows yet another embodiment of an applicator according to the invention placed over the distal end of an endoscope.

FIGS. 6B and 6C are examples of other possible embodiments of the applicator 50, indicated by the reference symbols 50' (FIG. 6B) and 50" (FIG. 6C), respectively. The difference between these embodiments and the applicator 50 of FIG. 6 is modifications in the actuation mechanism for releasing the optical element 202. For example, applicator 50' is shown to include a resilient strut or lever arm 68, wherein one end of the lever arm 68 may be attached to the base, and the other end of the lever arm 68 is in force-transmitting communication with a resilient tip 64a, which may be constructed similar to the tip 64 in FIG. 6A. Applicator 50" may include a dome-shaped membrane which may also include a tip 64b facing the optical element 202, with the tip 64b pushing the optical element 202 out of an opening against the optical port (in response to force exerted on membrane 68b), as analogously described above with reference to FIGS. 6 and 6A. Those skilled in the art will appreciate that other types of actuation mechanisms can be contemplated for use with the aforedescribed actuator, as long as an optical element can be precisely positioned over an optical port of an endoscope.

Figure 6D:
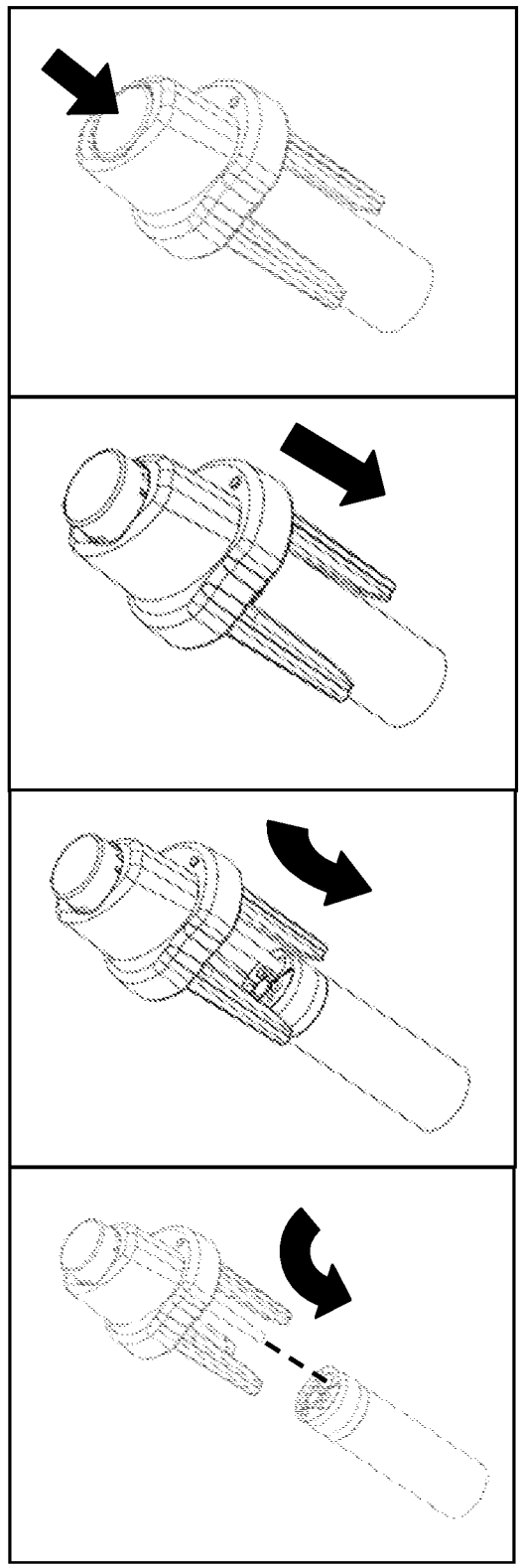
FIG. 6D shows sequential steps for applying an optical element on the distal end of an endoscope with the applicator of FIG. 5.

FIG. 6D illustrates a sequence of steps for positioning optical applicator 50, 50' or 50" on the distal end of the endoscope. One of the alignment members 514 (see FIG. 5) is pushed into, for example, working port 408, while the outside projections 512a, 512b grip around the periphery of the distal end. Referring now also back to FIGS. 5 and 6, for securely attaching filter 202 to the optical port or objective lens 404, an operator presses down on piston 518 in the direction indicated by arrow A. The compliant, rounded tip 64 then presses against the center of the non-adhesive side 202a of filter 202, also in the direction indicated by arrow A. Piston 518 then pushes filter 202 through the opening 62 against the optical port or objective lens 404, thereby ejecting the filter through the opening 62 towards the optical port 404. In one embodiment, the piston 518 may be composed of silicone rubber, but other suitable elastomer compounds can also be used. When the rounded tip of the piston 518 presses the filter 202 onto the endoscope objective lens in optical port 404, filter 202 contacts the endoscope objective from the center of the lens outwardly toward the periphery of the lens, thereby removing air bubbles trapped between the filter and the objective lens.

Figure 7:
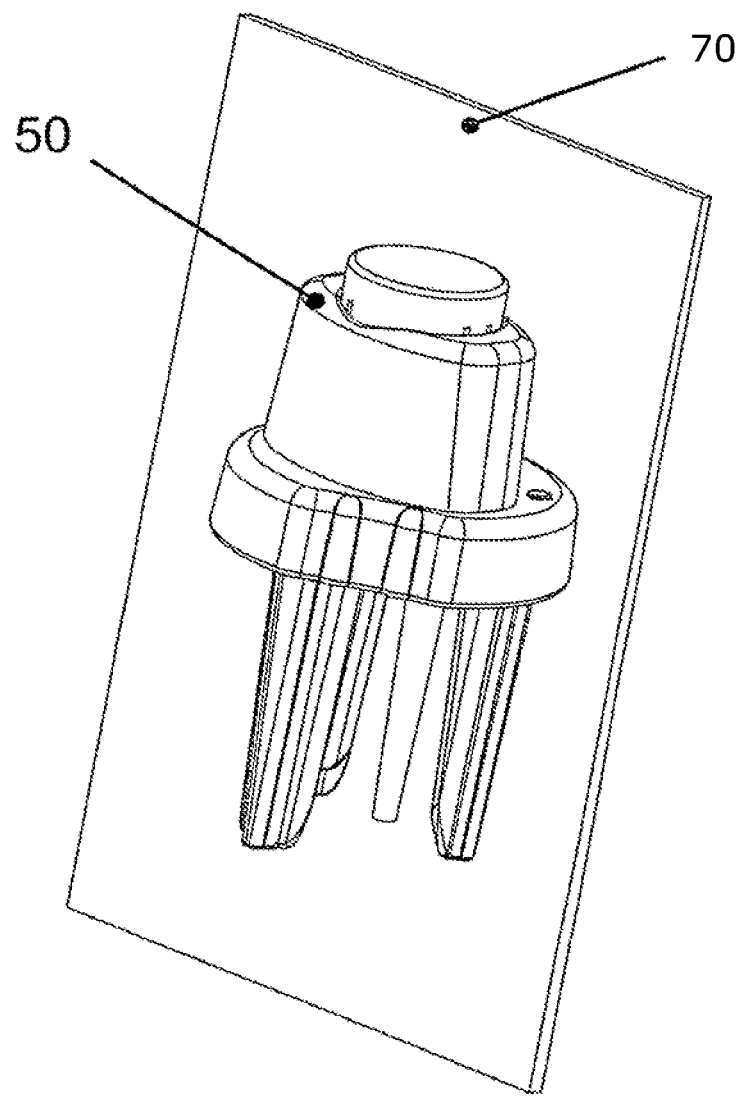
FIG. 7 shows the applicator according to the invention enclosed in a sterile package.

As shown in FIG. 7, applicator 50 is preferably preassembled with optical filter 202 and sealed in a sterile package 70. Prior to endoscopy, the applicator containing the filter 202 is removed from the sterile package 70 and positioned over the endoscope's distal end 402 (see FIG. 5). Applicator 50 is then pushed over distal end 402, with the interior projection(s) 514 engaging with the mating port(s) 408 and the outside projections 512a, 512b slidingly engaging with a portion of the exterior peripheral surface of distal end 402. The filter 202 is then applied to optical port 404 as described above.

Figure 8:
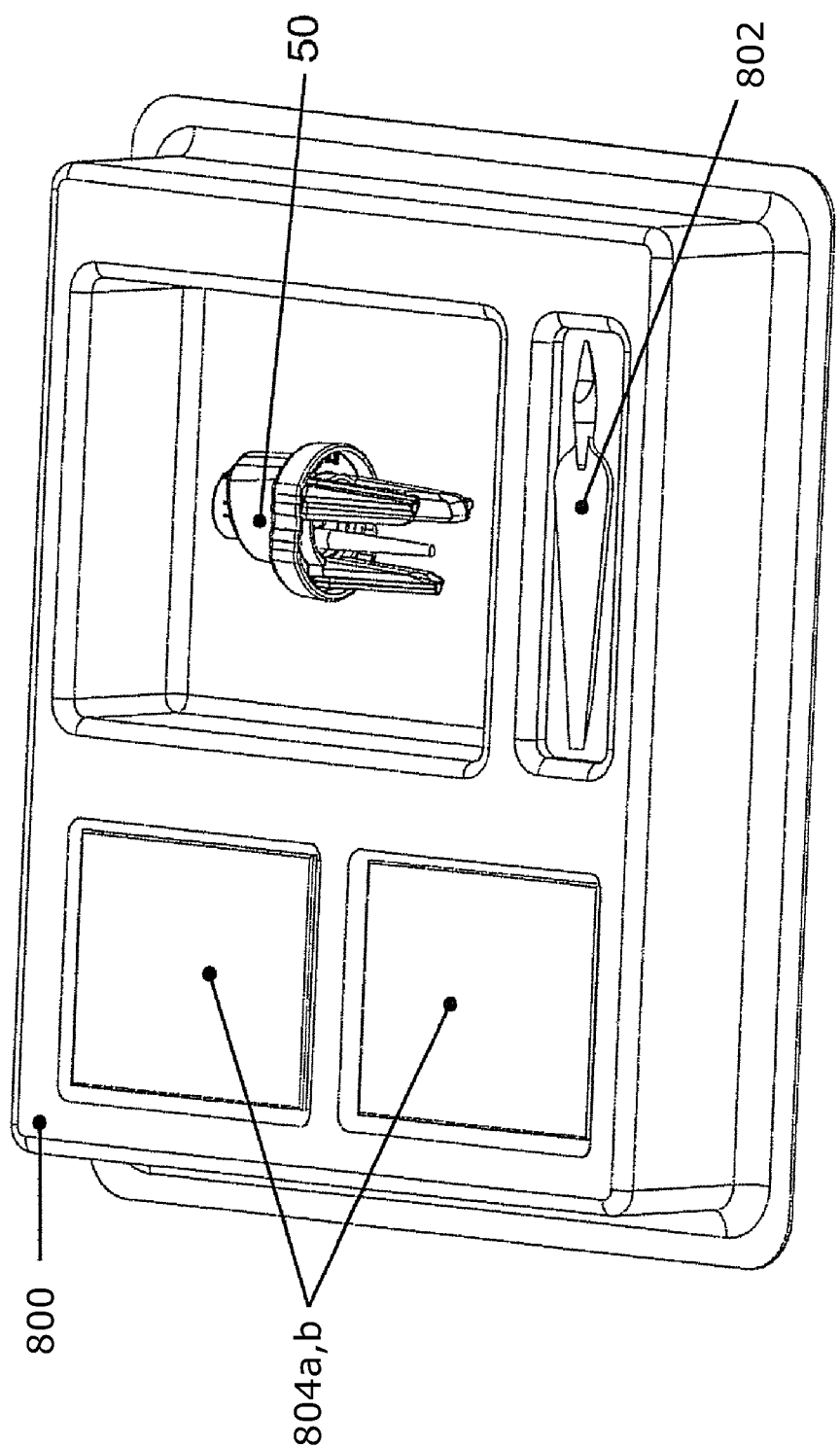
FIG. 8 shows a sterile kit with the applicator according to the invention and a filter cleaning and removal tool.

As shown in FIG. 8, applicator 50 may be supplied as a kit 800 which may include:

- A first solvent-impregnated swab or wipe 804a impregnated with a volatile solvent, such as alcohol or acetone, for preparing endoscope distal end 402 and removing any residue, oil or dust from the endoscope's optical port or objective lens 404 prior to application of filter 202;
- A removal tool 802 that aids in the removal of filter 802 after the endoscopy. A suitable tool is, for example, a plastic spatula-shaped instrument, such as a polypropylene nail cleaner/pick available from Qosina, Edgewood, N.Y.;
- A second solvent-impregnated swab, (e.g. an alcohol-impregnated wipe) 804b for removing residual adhesive or other contaminants from the endoscope objective lens after removal of filter 202 and prior to processing of the endoscope for reuse.

While the invention has been disclosed in connection with the preferred embodiments shown and described in detail, various modifications and improvements thereon will become readily apparent to those skilled in the art. For example, although not illustrated in the drawings, alignment may also be achieved by providing on the adapter of the invention recesses adapted to mate with features that protrude on the endoscope tip (such as port used to spray water across the objective lens to clear the lens) or by providing on the adapter a recess or projection adapted to engage with a complementary feature disposed, for example, along the periphery of the endoscope tip. Accordingly, the spirit and scope of the present invention is to be limited only by the following claims.

What is claimed is:

1. A method for attaching an optical element to an optical port disposed on a distal end of an endoscope comprising one or more registration features, comprising the steps of:
    providing an applicator releasably holding the optical element, said optical element having an adhesive side facing the endoscope's distal end and an opposing non-adhesive side, and said applicator comprising one or more alignment members;
    engaging one or more of the alignment members disposed on the applicator with the one or more corresponding registration features disposed at the endoscope's distal end, thereby aligning the optical element with the optical port, and
    applying with the applicator an external force against the non-adhesive side of the optical element so as to disengage the optical element from the applicator and urge the adhesive side of the optical element into contact with the optical port.

2. The method of claim 1, further comprising withdrawing the applicator from the distal end of the endoscope, while leaving the optical element attached to the optical port.

3. The method of claim 1, wherein applying an external force comprises actuating a yieldable element disposed in or on the applicator, said yieldable element being in force-transmitting communication with a non-adhesive side of the optical element.

4. The method of claim 1, wherein the one or more registration features are selected from the group consisting of a working port, a water port, an external peripheral surface, and a surface contour formed on the distal end.

5. The method of claim 1, further comprising cleaning the endoscope's optical port prior to placing the applicator on the distal end of the endoscope.

6. The method of claim 5, wherein cleaning comprises applying a volatile solvent to the endoscope's optical port.

7. The method of claim 1, further comprising removing the applicator from a sterile package.

* * * * *